US005709697A

United States Patent [19]
Ratcliff et al.

[11] Patent Number: 5,709,697
[45] Date of Patent: Jan. 20, 1998

[54] APPARATUS AND METHOD FOR REMOVING TISSUE

[75] Inventors: Keith Ratcliff, Newton; Salvatore Castro, Seymour; Dragomir C. Marinkovich, Sandy Hook, all of Conn.

[73] Assignee: United States Surgical Corporation, Norwalk, Conn.

[21] Appl. No.: 561,727

[22] Filed: Nov. 22, 1995

[51] Int. Cl.⁶ .................................................. A61B 17/32
[52] U.S. Cl. ........................ 606/180; 606/170; 606/167
[58] Field of Search ................... 606/159, 167, 606/170, 180; 128/749–754; 600/107

[56] References Cited

U.S. PATENT DOCUMENTS

| | | | |
|---|---|---|---|
| 1,568,008 | 12/1925 | Thomas . | |
| 1,609,456 | 12/1926 | Boyle . | |
| 1,901,731 | 3/1933 | Buerger | 600/107 |
| 2,117,278 | 5/1938 | Ainsworth . | |
| 2,541,542 | 2/1951 | Perez et al. . | |
| 3,320,957 | 5/1967 | Sokolik | 606/170 |
| 3,470,867 | 10/1969 | Goldsmith . | |
| 3,477,423 | 11/1969 | Griffith . | |
| 3,605,721 | 9/1971 | Hallac . | |
| 3,628,524 | 12/1971 | Jamshidi . | |
| 3,924,608 | 12/1975 | Mitsui | 606/107 |
| 4,099,518 | 7/1978 | Baylis et al. . | |
| 4,174,715 | 11/1979 | Hasson . | |
| 4,177,797 | 12/1979 | Baylis et al. | 128/754 |
| 4,306,570 | 12/1981 | Matthews | 128/754 |
| 4,461,305 | 7/1984 | Cibley | 128/754 |
| 4,651,752 | 3/1987 | Fuerst | 128/754 |
| 4,678,459 | 7/1987 | Onik et al. | 609/22 |
| 4,776,346 | 10/1988 | Beraha et al. | 128/754 |
| 4,785,826 | 11/1988 | Ward | 128/754 |
| 4,817,631 | 4/1989 | Schnepp-Pesch et al. | 128/753 |
| 4,850,373 | 7/1989 | Zatloukal et al. | 128/749 |
| 4,881,550 | 11/1989 | Kothe | 128/752 |

(List continued on next page.)

FOREIGN PATENT DOCUMENTS

| | | |
|---|---|---|
| 2610508 | 10/1987 | France . |
| 263228 | 8/1987 | Germany . |
| 1063653 | 3/1967 | Switzerland . |
| 534505 | 6/1970 | Switzerland . |

OTHER PUBLICATIONS

Biopsys Medical Inc., "Introducing The Singular Technology for Multi–Core Microcatcification Sampling", Circa Feb. 1995.

Ismet Hallac, M.D., "A New Design in Biopsy Needles", May 10, 1961, pp. 515–517.

Primary Examiner—Michael Buiz
Assistant Examiner—Patrick W. Rasche

[57] ABSTRACT

A surgical instrument for cutting tissue, which includes a housing, a cutting element movable between a retracted position disposed substantially within the housing and a deployed position extending outwardly from the housing, a guide member configured and dimensioned to direct orientation of the cutting element, operatively connected to the housing and defining a longitudinal axis, the guide member movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing. A method for surgically removing tissue is also provided and includes the steps of inserting an instrument into an incision formed at the operative site, deploying a blade guide at an angle relative to a longitudinal axis of the instrument, deploying a cutting element from a retracted position to an exposed position such that the cutting element is guided by the blade guide, moving the cutting element through a predetermined path such that a section of tissue is separated from the surrounding tissue, and removing the cut tissue from the surrounding tissue.

30 Claims, 13 Drawing Sheets

U.S. PATENT DOCUMENTS

| | | | |
|---|---|---|---|
| 4,926,877 | 5/1990 | Bookwalter | 128/754 |
| 4,940,061 | 7/1990 | Terwilliger et al. | 128/754 |
| 4,958,625 | 9/1990 | Bates et al. | 128/754 |
| 4,971,067 | 11/1990 | Bolduc et al. | 128/751 |
| 4,989,614 | 2/1991 | Dejter, Jr. et al. | 128/752 |
| 5,036,860 | 8/1991 | Leigh et al. | 128/754 |
| 5,111,828 | 5/1992 | Kornberg et al. | 128/754 |
| 5,122,134 | 6/1992 | Borzone et al. | 606/170 |
| 5,127,419 | 7/1992 | Kaldany | 128/754 |
| 5,133,360 | 7/1992 | Spears | 128/754 |
| 5,148,813 | 9/1992 | Bucalo | 128/754 |
| 5,197,484 | 3/1993 | Kornberg et al. | 128/754 |
| 5,224,488 | 7/1993 | Neuffer | 606/170 |
| 5,224,930 | 7/1993 | Spaeth et al. | 606/167 |
| 5,228,451 | 7/1993 | Bales et al. | 128/751 |
| 5,251,641 | 10/1993 | Xavier | 128/754 |
| 5,257,632 | 11/1993 | Turkel et al. | 128/754 |
| 5,271,414 | 12/1993 | Partika et al. | 128/754 |
| 5,289,520 | 2/1994 | Pellegrino et al. | 378/37 |
| 5,290,294 | 3/1994 | Cox et al. | 606/108 |
| 5,353,804 | 10/1994 | Kornberg et al. | 128/754 |
| 5,400,768 | 3/1995 | McNamara et al. | 606/170 |
| 5,462,062 | 10/1995 | Rubinstein et al. | 128/754 |
| 5,488,958 | 2/1996 | Tapel et al. | 128/754 |

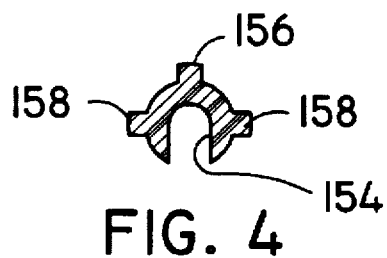
FIG. 4
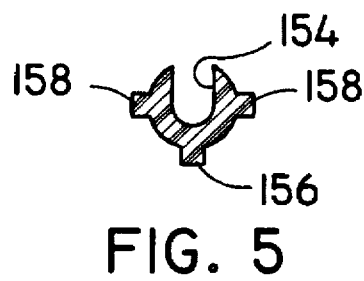
FIG. 5
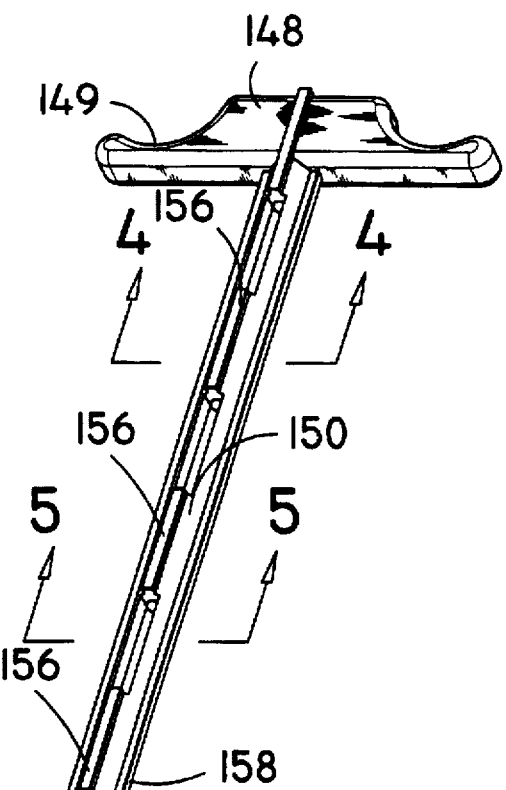
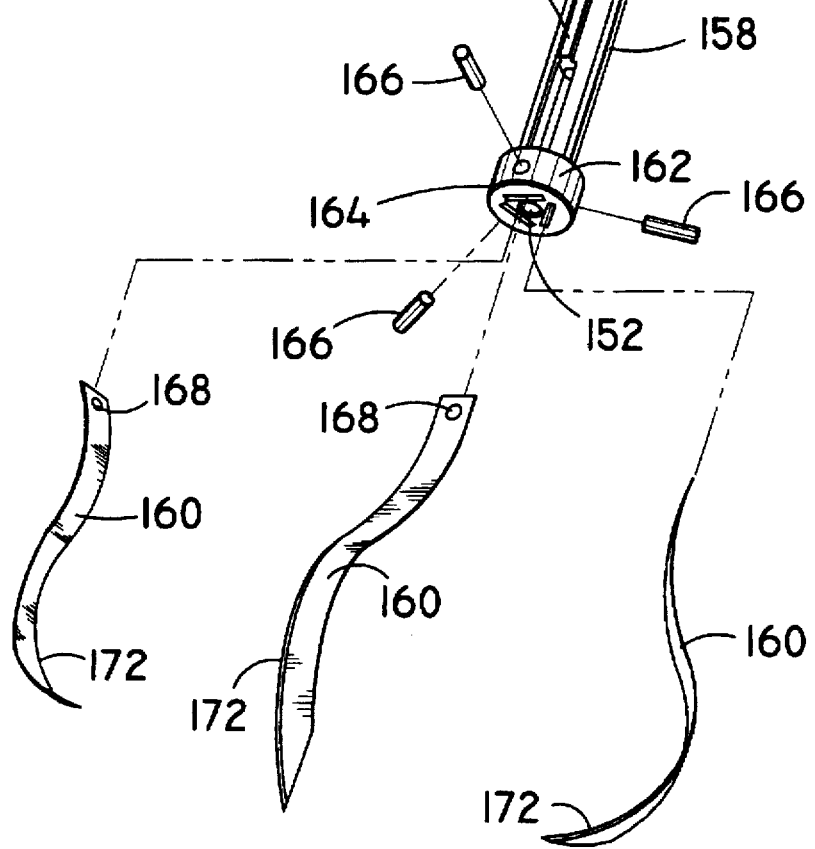
FIG. 3

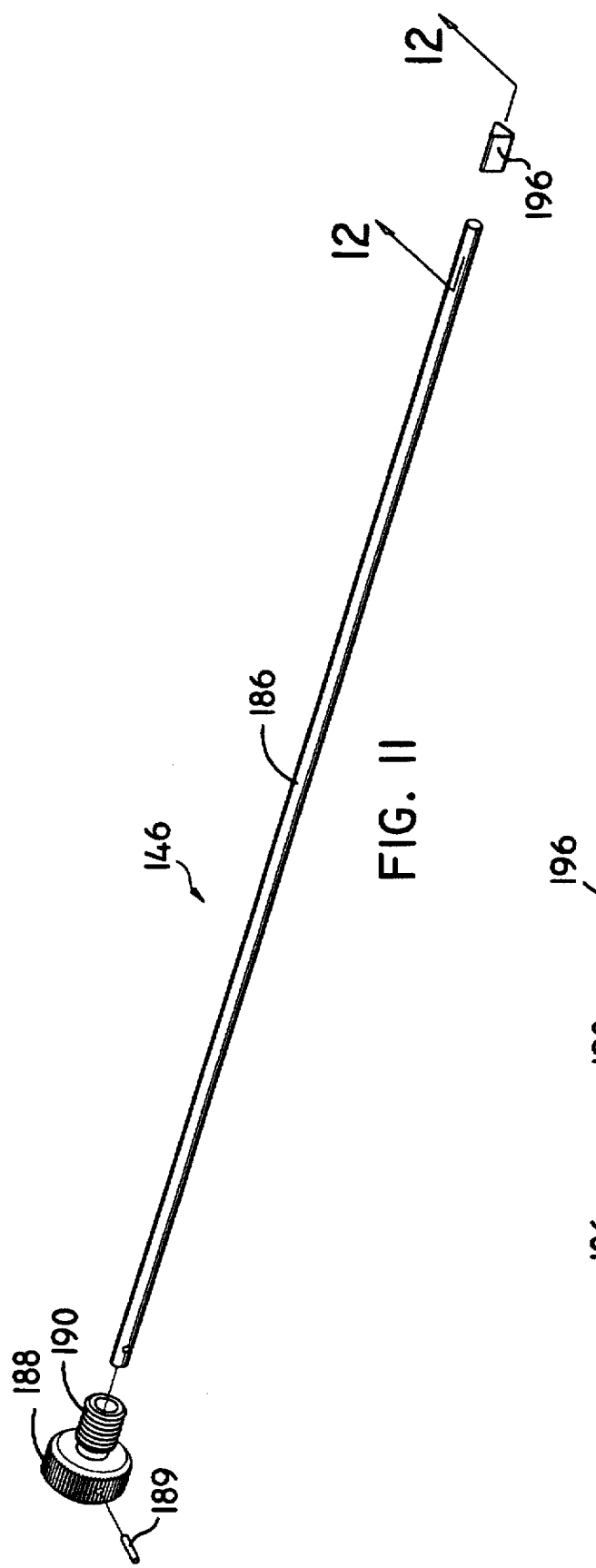
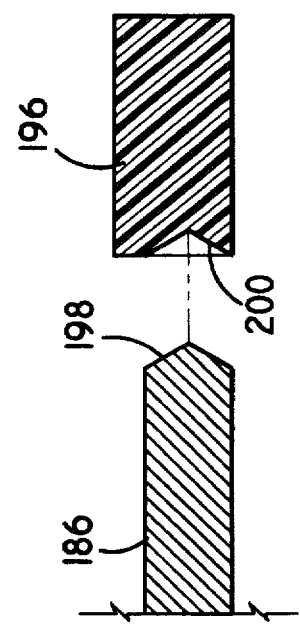
FIG. 11
FIG. 12

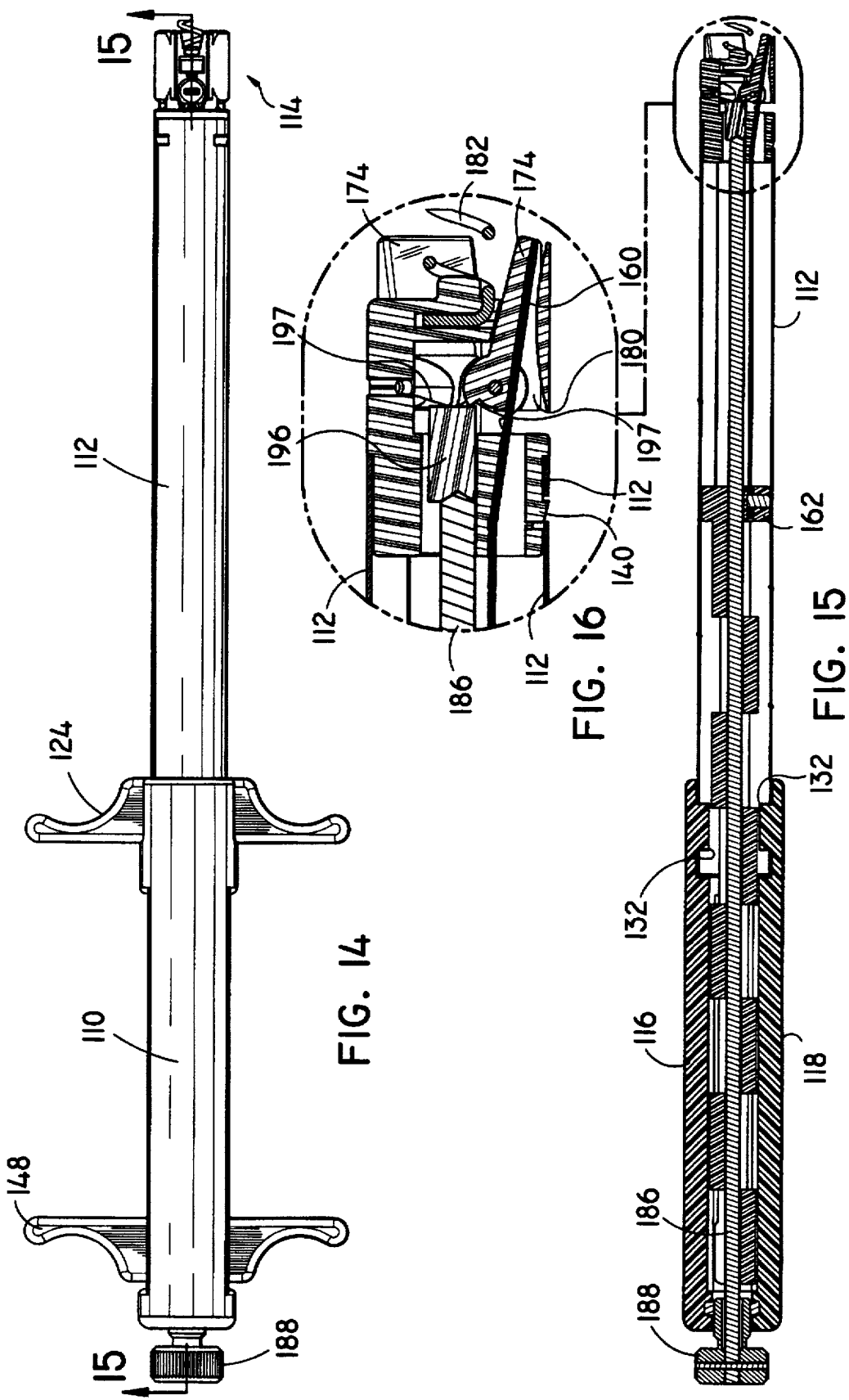

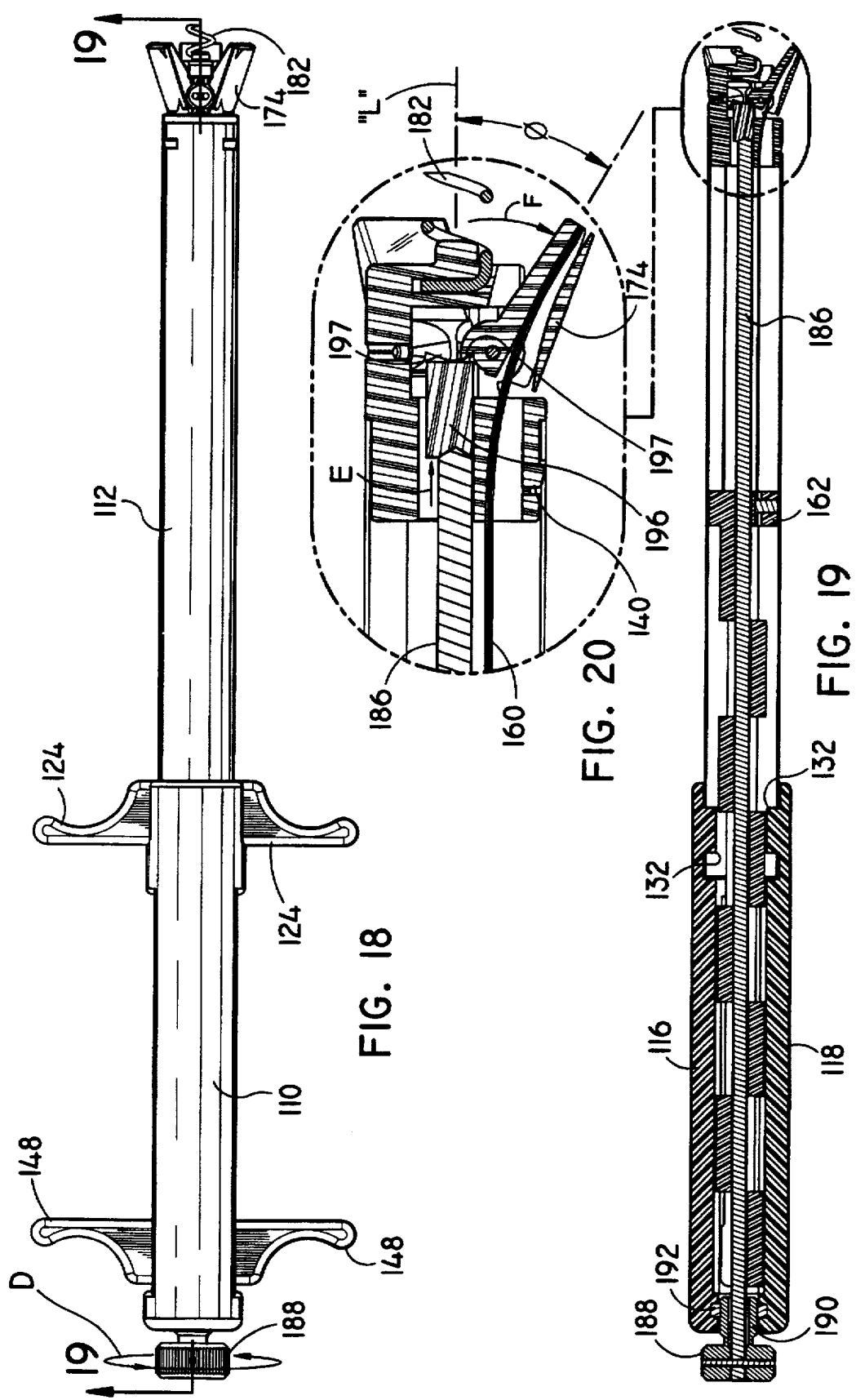

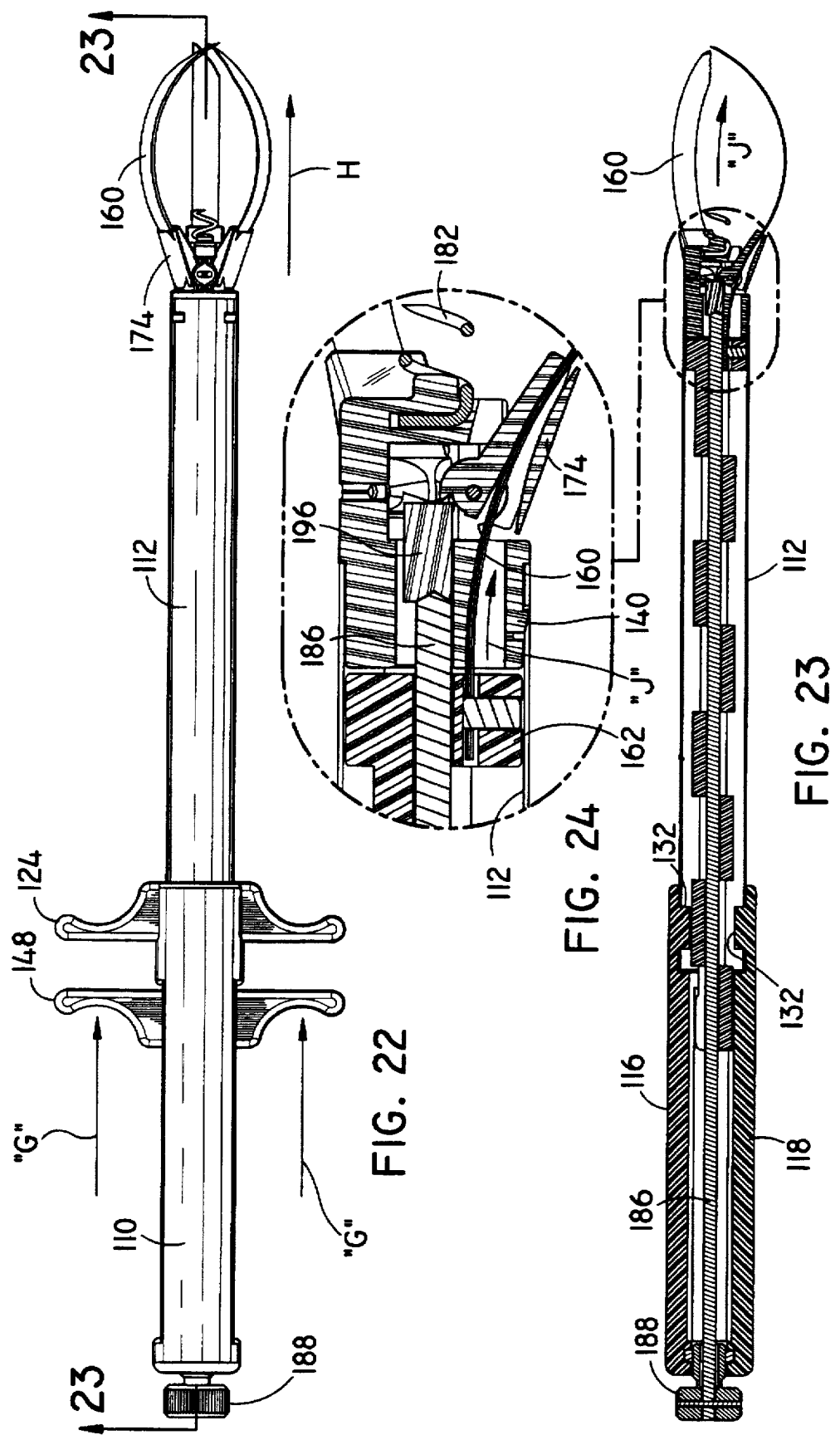

APPARATUS AND METHOD FOR REMOVING TISSUE

BACKGROUND

1. Technical Field

The present disclosure relates to apparatus and method for removal of tissue from within a patient's body. More particularly, the present disclosure relates to apparatus and method for percutaneous tissue removal.

2. Description of the Related Art

Numerous surgical instruments have been developed for performing minimally invasive surgical procedures. Such procedures greatly reduce recovery time for the patients in comparison to conventional open surgical procedures. Minimally invasive instruments also minimize damage to tissue surrounding the operative site. The enormous success of such instruments in procedures such as gall bladder removal and hernia repair has led to increased development of minimally invasive instruments for other operative procedures as well.

One area where minimally invasive instruments have begun to be utilized is in performing biopsies of suspect breast tissue to determine whether the tissue is malignant or benign. As is quite often the case, lesions within the breast are non-palpable, therefore, early diagnosis of suspect lesions in a patient's breast, which may be cancerous, has been greatly enhanced through the development of imaging machines, for example, stereotactic mammography imaging systems (hereafter referred to as "stereotactic machines"). In such machines, an elongated prone supporting examining table for x-ray mammography is provided with a central breast receiving aperture, through which the patient's pendulant breast is exposed to a horizontal beam of x-rays from a source which is angularly movable through an arc centered on the patient's breast permitting x-ray projection through more than 360 degrees around the patient's body. An example of such a stereotactic machine is disclosed in U.S. Pat. No. 5,289,520 which issued on Feb. 22, 1994 to Pellegrino et al., the contents of which are hereby incorporated by reference.

Fine needle biopsy is also facilitated by stereotactic machines. In such procedures, doctors can take advantage of the precision instrument positioning and suspect tissue position locating capabilities of the machine's imaging systems, to precisely insert a biopsy needle and retrieve a tissue sample.

However, minimally invasive instrumentation to remove target tissue to avoid open surgical techniques or potentially even mastectomy is not readily available. The present disclosure provides minimally invasive apparatus which are relatively easy to use and are inexpensive to manufacture and assemble. The present disclosure also provides methods for removing target tissue using such minimally invasive instrumentation.

SUMMARY

The present disclosure provides a surgical instrument for cutting tissue, which includes a housing, a cutting element movable between a retracted position disposed substantially within the housing and a deployed position extending outwardly from the housing, a guide member configured and dimensioned to direct orientation of the cutting element, operatively connected to the housing and defining a longitudinal axis, the guide member movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing.

In a preferred embodiment the cutting element is arcuately shaped. Alternatively and/or additionally, the cutting element may be a composite of a plurality of individual elements joined together. Also the instrument may include a plurality of cutting elements and a plurality of guide members. In such an embodiment, the plurality of guide members are preferably pivotably deployable. A cutting surface is preferably formed on at least one edge of the blade.

The instrument may also include a tissue retaining member positioned adjacent the guide member. In a preferred embodiment, the tissue retaining member is helically shaped such that upon rotation the tissue retaining element spirals through tissue which it contacts. The tissue retaining member may be fixedly mounted relative to the housing. Alternatively, the tissue retaining member may include a pair of graspers or like structure.

Another feature which may be provided on the instrument is an actuator operatively connected to the guide member and movable from a first position to a second position to selectively effect movement of the guide member from the first orientation to the second orientation. The actuator may be rotatably mounted relative to the housing.

A separate actuator may be provided which is operatively connected to the cutting element and movable from a first position to a second position to selectively effect movement of the cutting element from the retracted position to the deployed position. This actuator may be slidably mounted relative to the housing.

A method for surgically removing tissue is also provided and includes the steps of inserting an instrument into an incision formed at the operative site, deploying a blade guide at an angle relative to a longitudinal axis of the instrument, deploying a cutting element from a retracted position to an exposed position such that the cutting element is guided by the blade guide, moving the cutting element through a predetermined path such that a section of tissue is separated from the surrounding tissue, and removing the cut tissue from the surrounding tissue.

BRIEF DESCRIPTION OF THE DRAWINGS

Various embodiments are described herein with reference to the drawings, wherein:

FIG. 3 is a perspective view with parts separated of the cutting blade subassembly;

FIG. 4 is a cross-section view taken along section line 4—4 of FIG. 3;

FIG. 5 is a cross-section view taken along section line 5—5 of FIG. 3;

FIG. 11 is a perspective view with parts separated of the cutting blade guide actuator;

FIG. 12 is a partial cross-section view taken along section line 12—12 of FIG. 11;

FIG. 14 is a side view of the tissue removing instrument in an initial configuration;

FIG. 15 is a cross-section view taken along section line 15—15 of FIG. 14;

FIG. 16 is an enlarged view of the indicated area of detail in FIG. 15;

FIG. 18 is a side view of the instrument illustrating deployment of the blades' guides;

FIG. 19 is a cross-section view taken along section line 19—19 of FIG. 18;

FIG. 20 is an enlarged view of the indicated area of detail shown in FIG. 19;

FIG. 22 is a view similar to FIG. 18, which shows deployment of the cutting blades;

FIG. 23 is a cross-section view taken along section line 23—23 of FIG. 22;

FIG. 24 is an enlarged view of the indicated area of detail shown in FIG. 23;

DETAILED DESCRIPTION OF THE PREFERRED EMBODIMENTS

Figure 1:
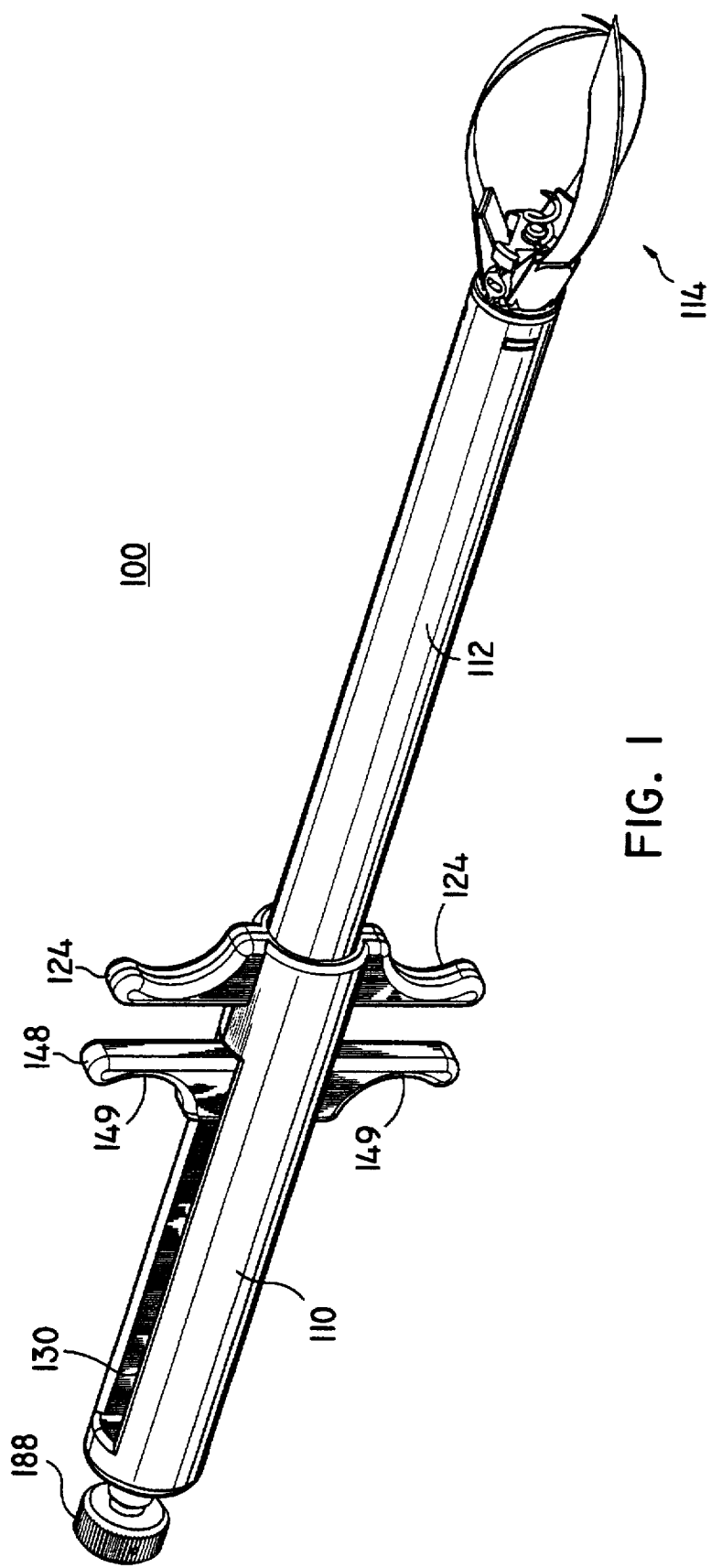
FIG. 1 is a perspective view of one embodiment of the tissue removing instrument of the present disclosure.
Figure 2:
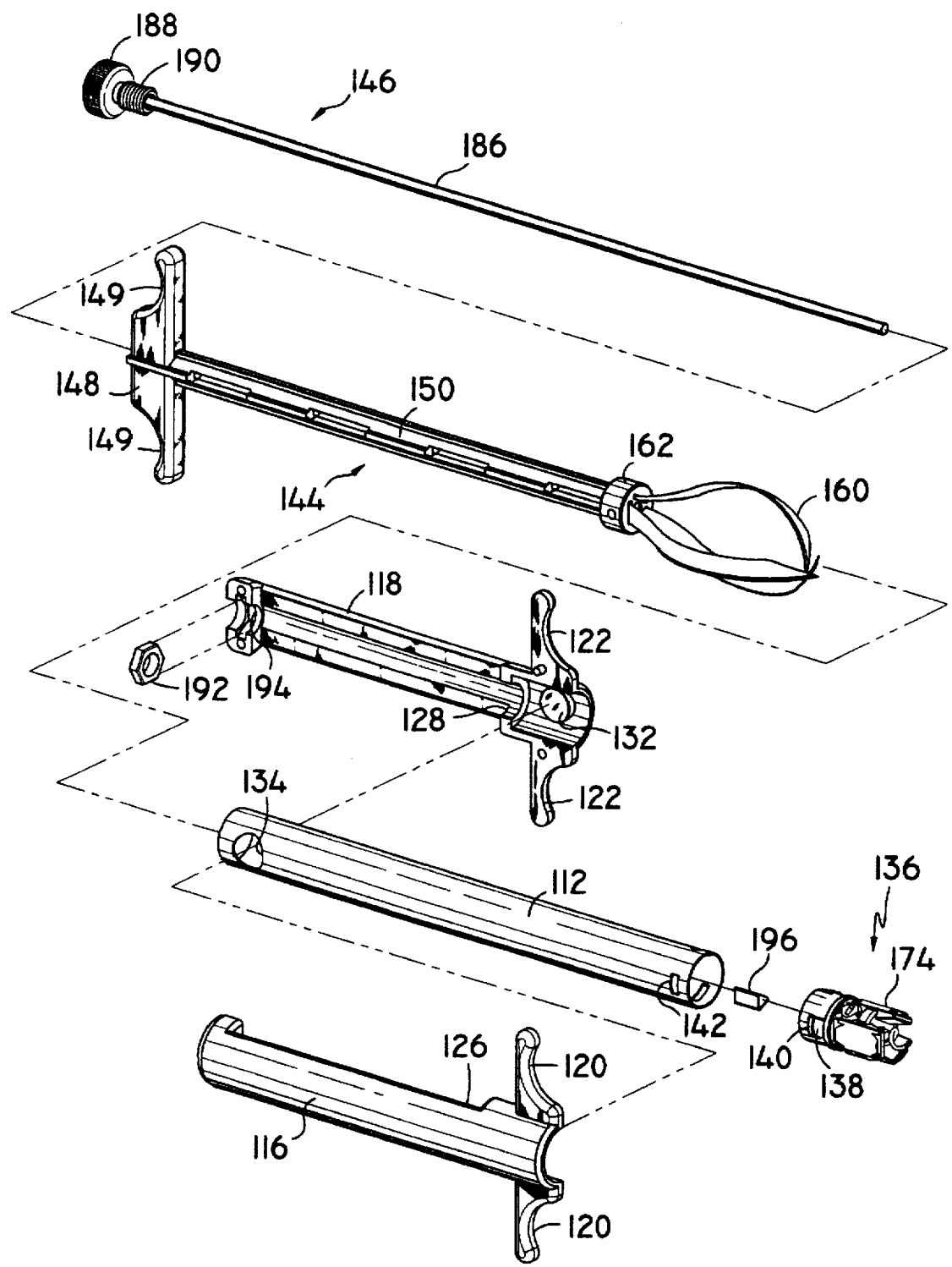
FIG. 2 is a perspective view with parts separated of the embodiment of FIG. 1.
Figure 6:
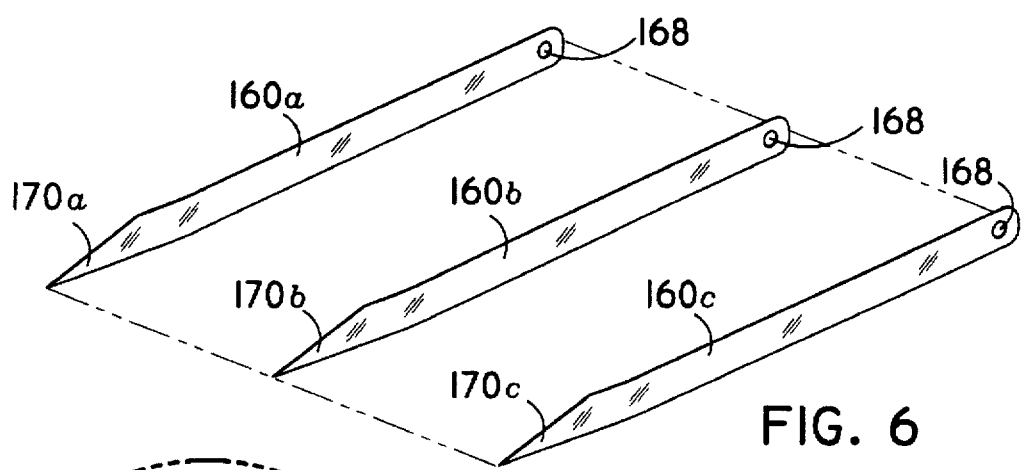
FIG. 6 is a perspective view with parts separated of the composite blade assembly of the embodiment of FIG. 1.
Figure 8:
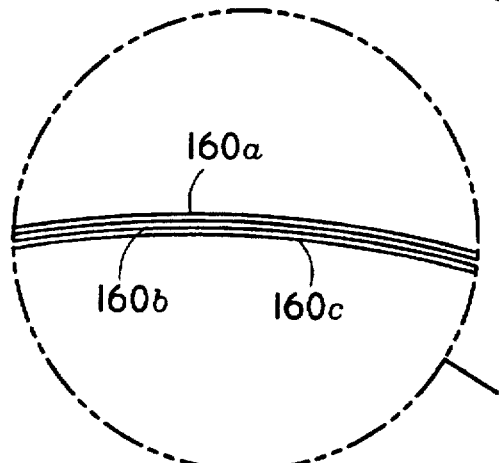
FIG. 8 is an enlarged view of the indicated area of detail of FIG. 7.
Figure 7:
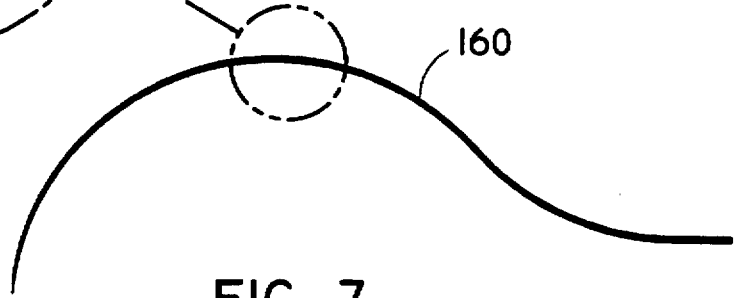
FIG. 7 is a side view of the composite blade assembly.
Figure 9:
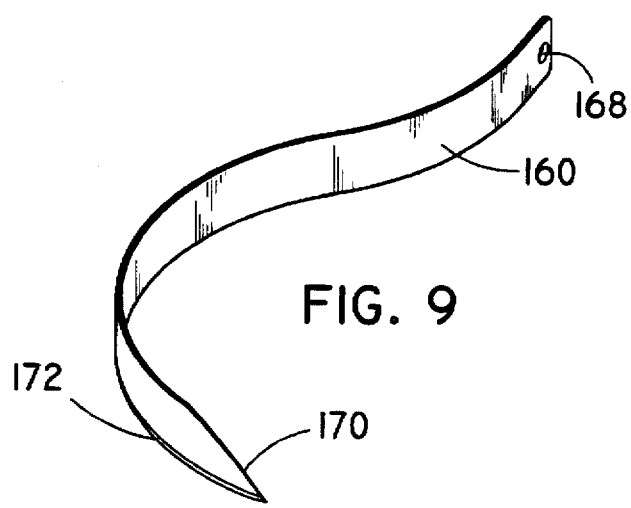
FIG. 9 is a perspective view of the composite cutting blade assembly.
Figure 10:
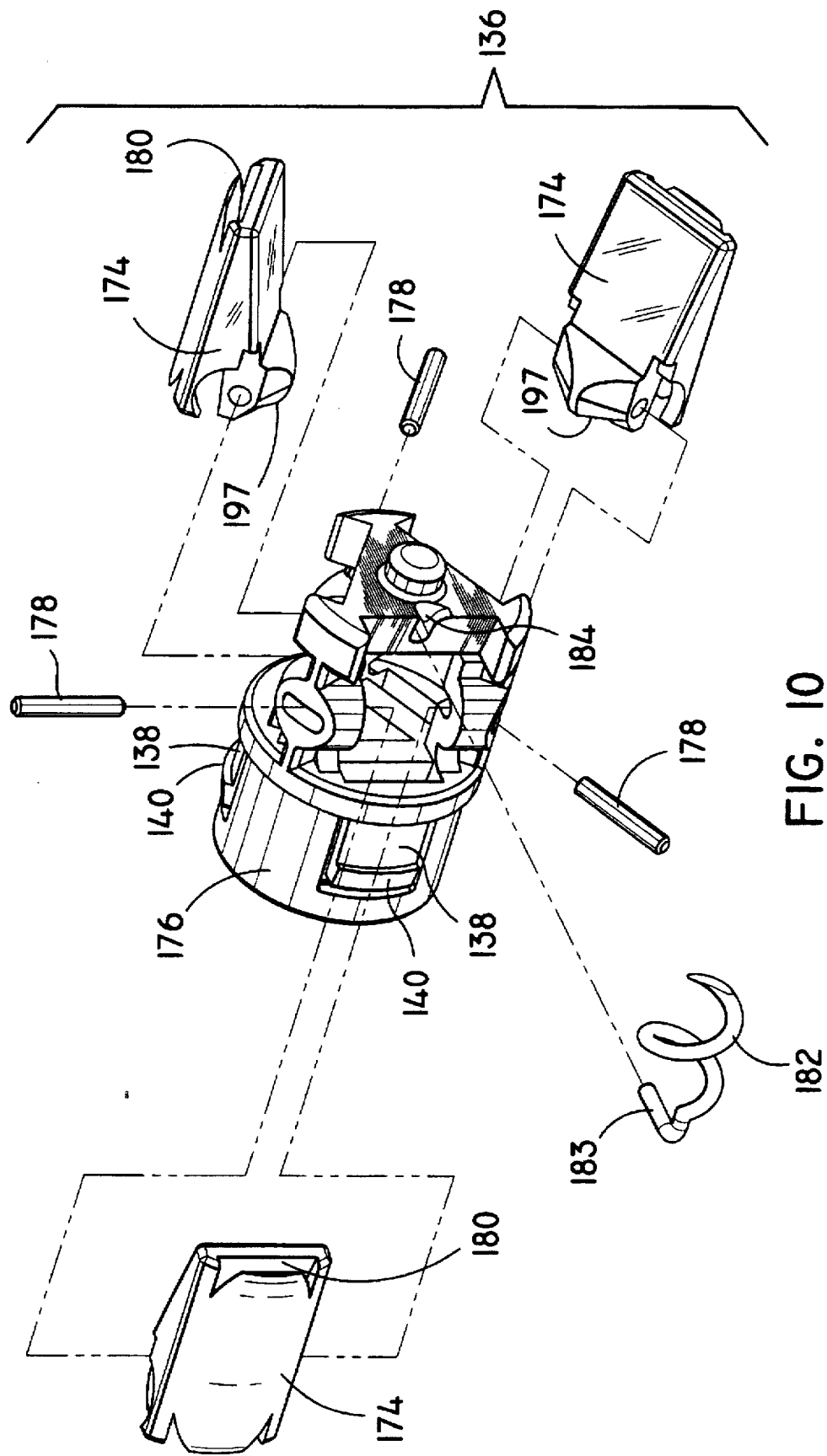
FIG. 10 is a perspective view of the distal end of the cutting blade guide assembly.
Figure 13:
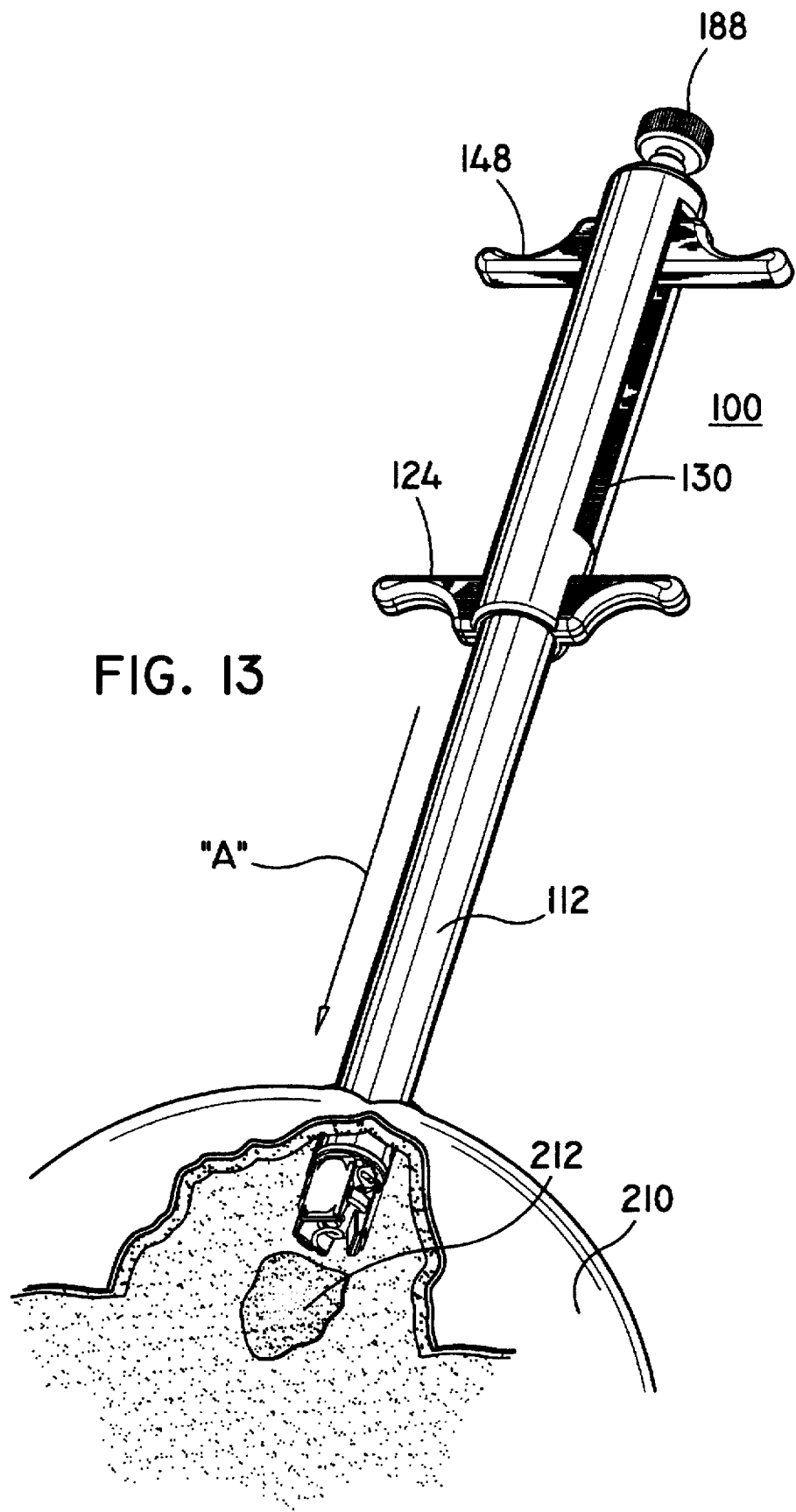
FIG. 13 is a perspective view of the tissue removing instrument being introduced into a patient.
Figure 17:
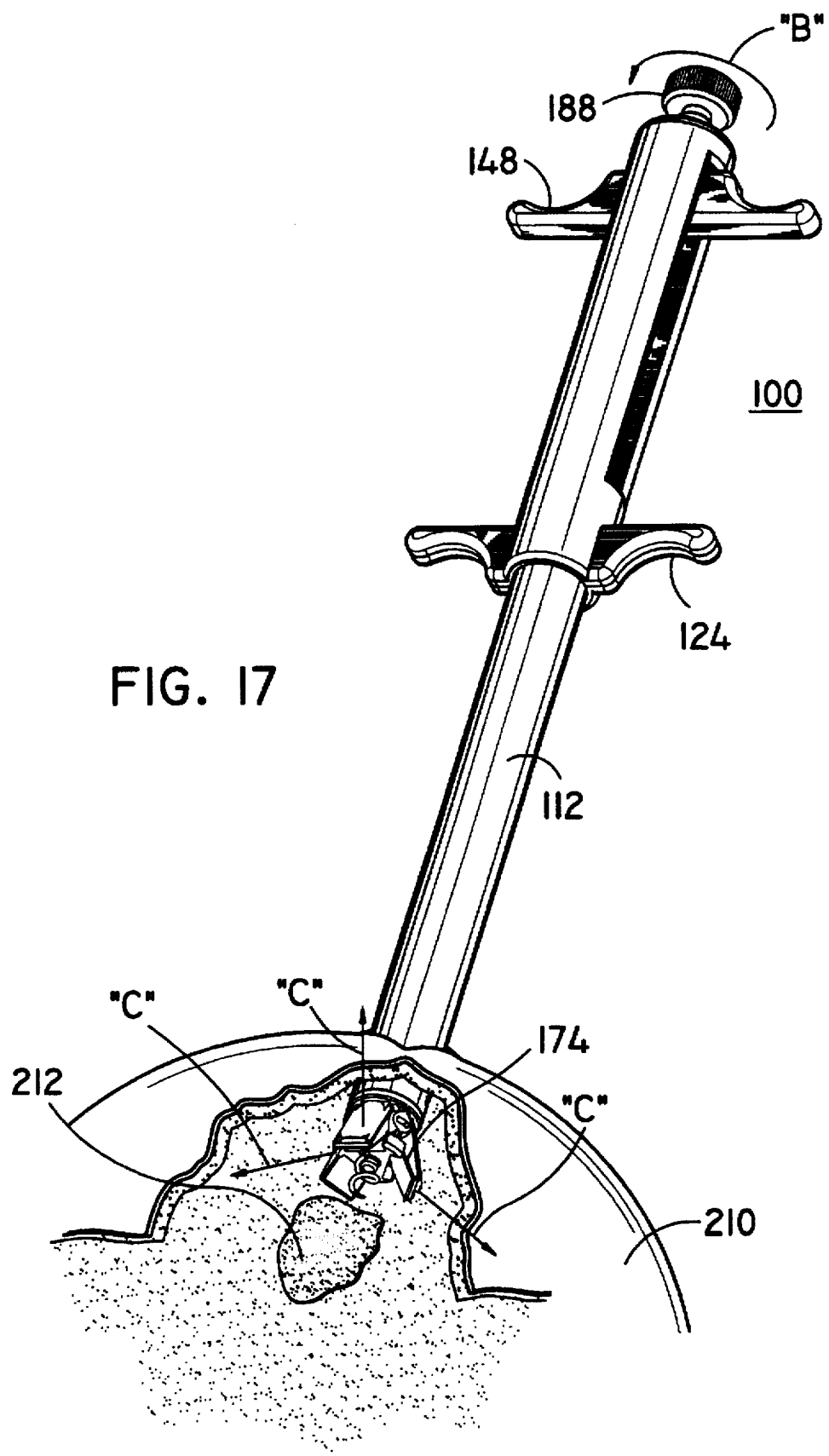
FIG. 17 is a further perspective view of the instrumentation in use illustrating deployment of the blade guides.

Referring initially to FIGS. 1 and 2, one embodiment of an instrument for removing target tissue in accordance with the present disclosure is designated by reference'numeral 100 throughout several views. Instrument 100 is particularly adapted for minimally invasive insertion into tissue immediately adjacent target tissue, isolating the target tissue from the surrounding tissue, cutting the tissue and removing the tissue from the patient. It will be understood by those skilled in the art, however, that the embodiments of the tissue removing instrument described herein, although directed to removal of breast tissue, may also be utilized for removing targeted tissue from other areas of a patient's body as well.

Generally, instrument 100 includes a housing or handle portion 110, an elongated tubular body portion 112 and a cutting head assembly 114. Except where noted otherwise, the materials utilized in the components of the instrument generally include such materials as polycarbonate for housing sections and related components, and stainless steel for components which transmit forces. One preferred polycarbonate material is available from General Electric under the trademark LEXAN. Radiolucent materials are also preferably utilized, as appropriate, for components which will be adjacent the target tissue so as not to interfere with imaging.

Handle 110 is formed from handle half-sections 116 and 118 which are preferably molded to have predetermined contoured regions for housing the various components of instrument 100 as well as facilitating the instrument's operation. Handle half-sections may be joined by any suitable techniques, such as snap fit connection, bonding, ultrasonic welding or by suitable adhesives. Grip portions 120 and 122 are provided on handle half-sections 116 and 118, respectively. Grip portions 120 and 122 preferably extend transversely away from a longitudinal axis of instrument 100 and are preferably contoured to be gripped by a single finger of the user. Handle half-sections 116 and 118 are provided with cut-out regions 126 and 128, respectively, so as to define elongated longitudinal slot 130 when the handle half-sections are joined.

Elongated tubular portion 112 is secured between the distal ends of handle half-sections 116 and 118, preferably by bores 132 formed on the inner wall portions of handle half-sections 116 and 118 being inserted in bores 134 formed near the proximal end of elongated tubular member 112. A blade guide assembly 136 is provided and is a subassembly of cutting head assembly 114. Blade guide assembly 136 is secured to the distal end of elongated tubular member 112, for example by flexible finger portions 138 having lip portions 140 which engage slots 142 formed near the distal end of elongated tubular member 112.

A cutting blade subassembly 144, which makes up a second subassembly of cutting head assembly 114, is slidably positioned within elongated tubular member 112. Actuator 146 is rotatably disposed within a longitudinal passageway formed in cutting blade assembly 144 as will be described further herein.

Referring now to FIG. 2 in conjunction with FIGS. 3–5, cutting blade assembly 144 is preferably provided with a grip 148 at the proximal end which includes contoured portions 149 to facilitate a positive gripping by the user upon actuation of instrument 100. A shaft 150 extends from grip 148 and, as noted above, preferably forms a longitudinal passageway 152 extending therethrough to receive actuator 146. Shaft 150 is preferably formed of a series of monolithically formed U-shaped longitudinal channel sections 154 and is provided with raised guide portions 156 and guide rails 158 to maintain the centrally disposed position of shaft 150 within elongated tubular member 112. This stabilization of shaft 150 is particularly important during reciprocating sliding movement of shaft 150 within elongated tubular member 112. A series of blades 160 are preferably preformed to have a predetermined curved configuration. Preferably the blades are made from either all stainless steel or a composite of stainless steel and a shape memory alloy. In the embodiment illustrated in FIG. 3, three such blades are provided and are secured to the base portion 162, for example by pins 166 being inserted through mounting holes formed on base 162 and passing through mounting holes 168 formed near the proximal ends of blades 160.

Referring to FIGS. 6–9, blades 160 are preferably formed as a composite of a multiple layers of individual blade portions, such as blade portions 160a, 160b and 160c being formed of the same configuration and dimensions. For example, the blade portions may be formed by stamping out from a sheet material or by other suitable known processes. Blade portions 160a, 160b, and 160c are preferably united by conventional techniques, such as bonding, welding, snap fit, adhesives or the like.

Blade guide assembly 136 is formed of individual blade guides 174 being pivotably mounted to a base 176, for example by pins 178 passing through transverse mounting bores formed on blade guides 174. Blade guides 174 are further provided with longitudinal slots 180 (as best seen in FIG. 16). Longitudinal slots 180 serve to direct blades 160 through blade guides 174 during actuation of the instrument.

Also provided on blade guide assembly 136 is a helically shaped tissue retaining member 182 which has a transversely extending leg portion 183 which is friction fit (interference fit) in an opening 184 formed near the distal end of blade guide assembly 136. Tissue retaining member 182 facilitates retaining the severed tissue in position at the distal end of instrument 100 during removal of the instrument from the patient.

Referring to FIGS. 11 and 12, blade guide assembly 136 is operated by actuator 146 which includes an elongated shaft 186 having a knob 188 secured to the proximal end of the shaft by, for example, pin 189. A threaded portion 190 is provided and extends from the distal end of knob 188 to facilitate relative reciprocating longitudinal movement of shaft 186 with respect to handle 110 by threaded engagement of threaded portion 190 with nut 192 (FIG. 2). Nut 192 is held fixed between handle half-sections 116 and 118 preferably by being seated in a molded portion, such as molded section 194. A pusher block 196 is provided and preferably has three flat surfaces so as to form a substantially triangular shaped cross-section such that the flat edges at the distal end of pusher block 196 bias against bearing surfaces 197 formed on blade guides 174 upon distal movement of actuator 146. This movement facilitates the pivotal deployment of blade guides 174. Shaft 186 is preferably provided with a conically shaped end portion 198 which mates with a seat portion 200 which is conformed to the conical shape of end portion 198 and is formed in the proximal end surface of pusher block 196 to facilitate sliding contact between the two pieces. This sliding contact facilitates longitudinally reciprocating movement of pusher block 196, which does not rotate with respect to blade guide assembly 136. Pusher block 196 is slidably positioned in a correspondingly shaped triangular opening formed in base 176 of blade guide assembly 136.

In operation, as illustrated in FIGS. 13–26, instrument 100 is inserted into the pendulant breast of the patient either through an incision formed at the site of the target tissue or through a trocar cannula inserted adjacent the target tissue 212. The patient's breast may be positioned in a pendulant fashion, for example by the patient lying prone on a conventional examination table having a breast-receiving aperture formed thereon or on such a table provided with an imaging machine, e.g., a stereotactic machine.

FIGS. 14–16 illustrate the initial configuration of instrument 100 upon insertion into the patient. In particular, blade guides 174 are shown in their fully retracted position aligned longitudinally with elongated tubular member 112 to facilitate insertion of the instrument into the patient. As shown in FIGS. 17–20, once instrument 100 is positioned at the desired location, blade guides 170 are deployed to the desired angle by rotating knob 188 in a clockwise fashion as indicated by arrow "B" in FIG. 17 and arrow "D" in FIG. 18. Upon such rotational movement of knob 188, blade guides 174 deploy radially outward as indicated by arrows "C" in FIG. 17 and arrow "F" in FIG. 20. This deployment is facilitated by the threading of threaded portion 190 and nut 192 causing distal movement of shaft 186 as indicated by arrow "E" in FIG. 20. Shaft 186 urges pusher block to push against bearing surfaces 197 thereby pivoting blade guides 174 outwardly. Blade guides 174 are preferably deployed to a predetermined angle "φ", with respect to central longitudinal axis "L" as shown in FIG. 20. One particularly effective angle of deployment relative to the central longitudinal axis "L" has been found to be approximately 25'.

Figure 21:
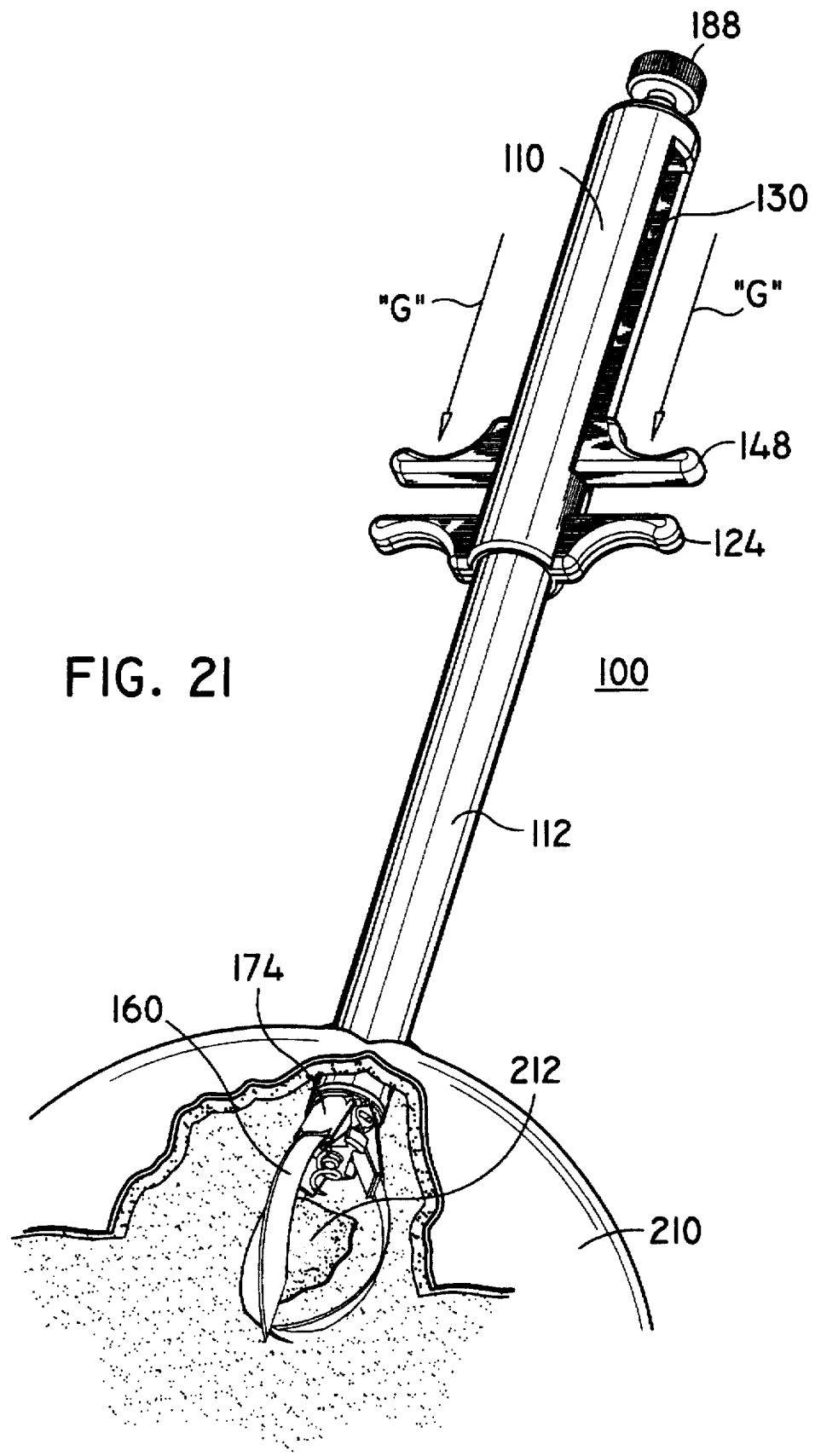
FIG. 21 is a further perspective view of the instrument in use illustrating deployment of the cutting blades of the tissue removing instrument.

Blades 160 are deployed by moving grip 148 in a distal direction as indicated by arrows "G" in FIGS. 21 and 22. In this manner, blades 160 exit the distal ends of blade guides 174, indicated by arrows "J" in FIGS. 23 and 24, at an initial angle φ relative to the central longitudinal axis "L" of instrument 100. The preformed curvature of blades 160 causes the blades to travel through a predetermined arc slicing through the tissue and to converge at a point spaced from the distal end of instrument 100 thus, surrounding the target tissue 212. With blades 160 in the fully deployed position, the user then rotates instrument 100 in the clockwise fashion as indicated by arrows "T" in FIG. 25. Preferably instrument 100 is rotated at least slightly greater than 120' for the embodiment shown having three blades 160 to form a complete cut of the tissue surrounding the target tissue. This rotational motion of instrument 100 causes blades 160 to rotate in a clockwise fashion such that cutting edges 172 cut away a solid section of tissue enclosed by blades 160.

Figure 26:
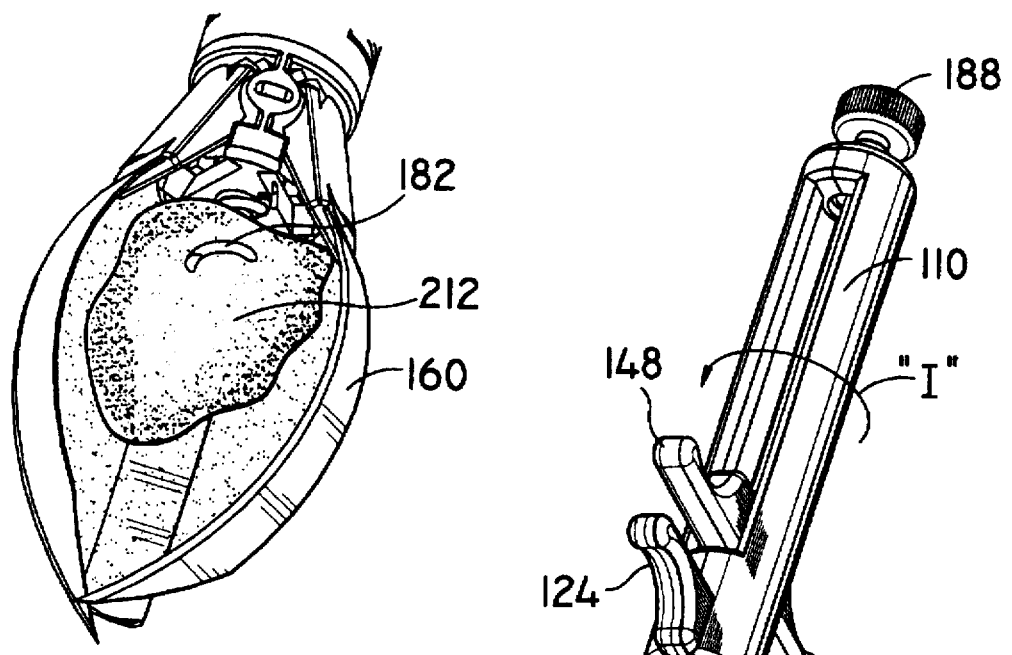
FIG. 26 is an enlarged view of the distal end of the instrument with the severed tissue contained therein.
Figure 25:
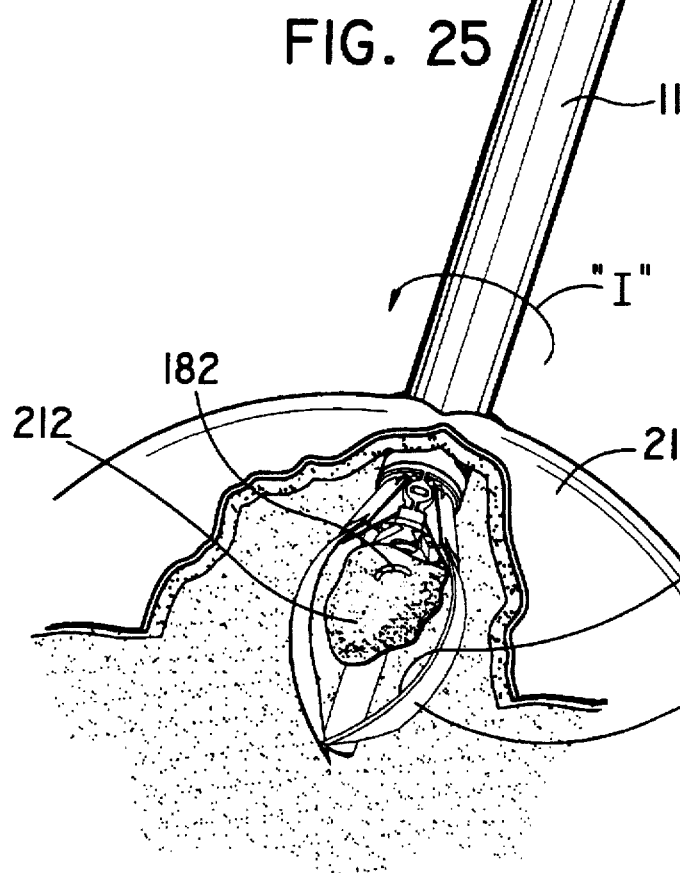
FIG. 25 is a further perspective view of the instrument in use illustrating rotational cutting of the blades.

As instrument 100 is rotated, helically shaped tissue retaining member 182 rotates spirally through the target tissue 212 to secure the tissue to instrument 100 as shown in FIGS. 25 and 26. With the target tissue 212 firmly retained at the distal end of instrument 100 within blades 160, instrument 100 may be removed from the patient's body. In certain instances, it may be desirable for blades 160 to be retracted by the user, i.e., by pulling back upon grip 148 and rotating knob 188 in a counterclockwise fashion, to realign blade guides 174 with the central longitudinal axis "L" of instrument 100 to facilitate removal of the instrument from the patient.

It will be understood that various modifications may be made to the embodiments disclosed herein. Therefore, the above description should not be construed as limiting, but merely as an exemplification of a preferred embodiment. Those skilled in the art will envision other modifications within the scope and spirit of the claims appended hereto.

What is claimed is:

1. A surgical instrument for cutting tissue, which comprises: a housing;
   a cutting blade having a variable configuration movable between a retracted position disposed substantially within the housing wherein the cutting blade assumes a first configuration and a deployed position extending outwardly from the housing wherein the cutting blade assumes a second configuration different from the first configuration; and
   a guide member configured and dimensioned to direct orientation of the cutting blade, operatively connected to the housing and defining a longitudinal axis, the guide member movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing.

2. A surgical instrument according to claim 1, wherein the cutting element is arcuately shaped.

3. A surgical instrument according to claim 1, wherein the cutting element is a composite of a plurality of individual elements joined together.

4. A surgical instrument according to claim 1, wherein the cutting element is a blade having a cutting surface formed on at least one edge of the blade.

5. A surgical instrument according to claim 1, which further comprises a tissue retaining member positioned adjacent the guide member.

6. A surgical instrument according to claim 5, wherein the tissue retaining member is helically shaped such that upon rotation the tissue retaining element spirals through tissue which it contacts.

7. A surgical instrument according to claim 5, wherein the tissue retaining member is fixedly mounted relative to the housing.

8. A surgical instrument according to claim 1, which further comprises an actuator operatively connected to the guide member and movable from a first position to a second position to selectively effect movement of the guide member from the first orientation to the second orientation.

9. A surgical instrument according to claim 8, wherein the actuator is rotatably mounted relative to the housing.

10. A surgical instrument according to claim 1, which further comprises an actuator operatively connected to the cutting element and movable from a first position to a second position to selectively effect movement of the cutting element from the retracted position to the deployed position.

11. A surgical instrument according to claim 10, wherein the actuator is slidably mounted relative to the housing.

12. A surgical instrument for cutting tissue, which comprises:
   a housing;
   a plurality of cutting elements movable between a retracted position disposed substantially within the housing and a deployed position extending outwardly from the housing; and
   a plurality of guide members configured and dimensioned to direct orientation of the plurality of cutting elements, operatively connected to the housing and defining a longitudinal axis, the plurality of guide members being movable from a first orientation wherein the longitudinal axis of at least one of the plurality of guide members is aligned with a longitudinal axis of the housing, to a second orientation wherein the longitudinal axis of the at least one guide member is oriented at a predetermined angle relative to the longitudinal axis of the housing.

13. A surgical instrument according to claim 12, wherein the plurality of guide members are pivotably deployable.

14. A surgical instrument for cutting tissue, which comprises:
   a handle portion;
   a cutting blade having a variable configuration and being operatively associated with the handle portion and movable between a retracted position wherein the cutting blade assumes a first configuration and a deployed position wherein the cutting blade assumes a second configuration different from the first configuration;
   a guide member configured and dimensioned to direct orientation of the cutting blade, operatively associated with the handle portion and defining a longitudinal axis, the guide member movable from a first position wherein the longitudinal axis of the guide member is aligned with a longitudinal axis of the housing to a second position wherein the longitudinal axis of the guide member is oriented at a predetermined angle relative to the longitudinal axis of the housing; and
   a tissue retaining member positioned adjacent the guide member and adapted to engage tissue such that the tissue is retained adjacent the guide member.

15. A surgical instrument according to claim 14, wherein the cutting element is arcuately shaped.

16. A surgical instrument according to claim 14, wherein the cutting element is a composite of a plurality of individual elements joined together.

17. A surgical instrument according to claim 14, wherein the cutting element is a blade having a cutting surface formed on at least one edge of the blade.

18. A surgical instrument according to claim 14, wherein the tissue retaining member is helically shaped such that upon rotation the tissue retaining element spirals through tissue which it contacts.

19. A surgical instrument according to claim 18, wherein the tissue retaining member is fixedly mounted relative to the housing.

20. A surgical instrument according to claim 14, which further comprises an actuator operatively connected to the guide member and movable from a first position to a second position to selectively effect movement of the guide member from the first orientation to the second orientation.

21. A surgical instrument according to claim 20, wherein the actuator is rotatably mounted relative to the housing.

22. A surgical instrument according to claim 14, which further comprises an actuator operatively connected to the cutting element and movable from a first position to a second position to selectively effect movement of the cutting element from the retracted position to the deployed position.

23. A surgical instrument according to claim 22, wherein the actuator is slidably mounted relative to the housing.

24. A surgical instrument which comprises:
   a handle portion;
   a plurality of cutting elements operatively associated with the handle portion and movable between a retracted position and a deployed position;
   a plurality of guide members configured and dimensioned to direct orientation of the plurality of cutting elements, operatively associated with the handle portion and defining a longitudinal axis, at least one of the plurality of guide members movable from a first position wherein the longitudinal axis of the at least one guide member is aligned with a longitudinal axis of the housing to a second position wherein the longitudinal axis of the at least one guide member is oriented at a predetermined angle relative to the longitudinal axis of the housing; and
   a tissue retaining member positioned adjacent the plurality of guide members and adapted to engage tissue such that the tissue is retained adjacent the guide member.

25. A surgical instrument according to claim 17, wherein the plurality of guide members are pivotably deployable.

26. A method for surgically removing tissue comprising the steps of:
   inserting an instrument into an incision formed at the operative site;
   deploying a blade guide at an angle relative to a longitudinal axis of the instrument;
   deploying a cutting blade from a retracted position wherein the cutting blade assumes a first configuration to an exposed position such that the cutting blade is guided by the blade guide and assumes a second configuration different from the first configuration;
   moving the cutting blade through a predetermined path such that a section of tissue is separated from the surrounding tissue; and
   removing the cut tissue from the surrounding tissue.

27. A surgical instrument for cutting tissue, which comprises:
   a housing;
   a cutting element movable between a retracted position disposed substantially within the housing and a deployed position extending outwardly from the housing; and
   a guide member defining a passageway therethrough to direct orientation of the cutting element through the passageway, the guide member being operatively connected to the housing and defining a longitudinal axis, the guide member being movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing.

28. A surgical instrument for cutting tissue, which comprises:

- a housing;
- a flexible cutting blade movable between a retracted position wherein the flexible cutting blade assumes a first configuration disposed substantially within the housing and a deployed position wherein the flexible cutting blade assumes a second configuration extending outwardly from the housing; and
- a guide member configured and dimensioned to direct orientation of the cutting edge, operatively connected to the housing and defining a longitudinal axis, the guide member movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing.

29. A surgical instrument for cutting tissue, which comprises:

- a housing;
- a flexible cutting blade movable between a retracted position disposed substantially within the housing along an arcuate path wherein the cutting blade assumes a second configuration different from the first configuration and a deployed position extending outwardly from the housing, the cutting blade defining a cutting edge formed along at least one side thereof and being rotatable about a central longitudinal axis of the surgical instrument; and
- a guide member configured and dimensioned to direct orientation of the cutting element, operatively connected to the housing and defining a longitudinal axis, the guide member movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing.

30. A surgical instrument for cutting tissue, which comprises:

- a housing;
- a guide member fixedly connected to a distal end of the housing and defining a passageway therethrough and having a longitudinal axis, a portion of the guide member movable from a first orientation wherein the longitudinal axis of the guide member is aligned with a longitudinal axis of the housing to a second orientation wherein the longitudinal axis of the guide member is oriented at a predetermined angle relative to the longitudinal axis of the housing;
- an elongated cutting blade slidable through the passageway of the guide member between a retracted position disposed substantially within the housing and a deployed position extending outwardly from the housing; and
- wherein the housing includes an actuator actuable to move the elongated cutting blade between the retracted and deployed positions.

* * * * *